(12) United States Patent
Nousiainen

(10) Patent No.: US 11,564,589 B2
(45) Date of Patent: Jan. 31, 2023

(54) PATIENT TABLE ASSEMBLY

(71) Applicant: KONINKLIJKE PHILIPS N.V., Eindhoven (NL)

(72) Inventor: Jere Matti Nousiainen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1212 days.

(21) Appl. No.: 15/552,362

(22) PCT Filed: Mar. 4, 2016

(86) PCT No.: PCT/EP2016/054676
§ 371 (c)(1),
(2) Date: Aug. 21, 2017

(87) PCT Pub. No.: WO2016/139352
PCT Pub. Date: Sep. 9, 2016

(65) Prior Publication Data
US 2018/0035911 A1    Feb. 8, 2018

Related U.S. Application Data

(60) Provisional application No. 62/128,073, filed on Mar. 4, 2015.

(30) Foreign Application Priority Data

Jul. 31, 2015   (EP) ..................................... 15179258

(51) Int. Cl.
*A61B 5/055*    (2006.01)
*G01R 33/34*    (2006.01)
*A61B 6/00*    (2006.01)

(52) U.S. Cl.
CPC ................ *A61B 5/055* (2013.01); *A61B 6/44* (2013.01); *G01R 33/34007* (2013.01); *G01R 33/34084* (2013.01)

(58) Field of Classification Search
CPC .......... A61N 5/1049; A61N 2005/1097; A61G 13/12; A61G 13/125; A61G 13/122;
(Continued)

(56) References Cited

U.S. PATENT DOCUMENTS 3,742,528 A   7/1973   Munch
3,947,686 A   3/1976   Cooper
(Continued)

FOREIGN PATENT DOCUMENTS

CN   202537529 U   11/2012
JP   63264051   10/1988
(Continued)

*Primary Examiner* — Catherine B Kuhlman
*Assistant Examiner* — Sean A Frith

(57) ABSTRACT

A patient table comprises: a curved base plate, a support face arranged over the curved base plate's concave side, a planar table top removable placed over the support face surface and the planar table top having a flat support surface opposite form the support face; the planar table top being contiguous to the support face. In particular in the patient table assembly with longitudinal sides (a) longitudinal groove(s) are provided along one or both the longitudinal sides in the flat support surface and at the longitudinal groove(s) indentations, in particular notches, are provided in the flat support surface and transverse to the groove(s).

16 Claims, 18 Drawing Sheets

(58) Field of Classification Search
CPC .............. A61G 13/1255; A61G 13/123; A61G 13/1245; A61G 2210/50; A61F 5/3769; A61B 90/57; A61B 90/50; A61B 90/14; A61B 2090/571

See application file for complete search history.

(56) References Cited

U.S. PATENT DOCUMENTS

| | | | |
|---|---|---|---|
| 5,475,884 A | 12/1995 | Kirmse | |
| 5,493,741 A | 2/1996 | Baer | |
| 5,806,116 A | 9/1998 | Oliver et al. | |
| 6,377,830 B1 | 4/2002 | Carrozzi | |
| 6,493,417 B1 | 12/2002 | Baer | |
| 6,616,237 B2 | 9/2003 | Sonner et al. | |
| 7,257,849 B2* | 8/2007 | Jahrling | A61B 6/0442 5/81.1 R |
| 7,603,164 B2 | 10/2009 | Uematsu | |
| 7,701,209 B1* | 4/2010 | Green | G01R 33/307 324/318 |
| 7,869,857 B2 | 1/2011 | Satragno | |
| 2004/0143905 A1* | 7/2004 | Pastyr | A61B 6/0442 5/601 |
| 2004/0255383 A1* | 12/2004 | Longton | A61B 6/0442 5/601 |
| 2007/0191706 A1 | 8/2007 | Calderon et al. | |
| 2008/0191696 A1 | 8/2008 | Van Der Burgt | |
| 2009/0211027 A1 | 8/2009 | Dimmer | |
| 2009/0306494 A1 | 12/2009 | Scarth | |
| 2009/0306495 A1 | 12/2009 | Scarth | |
| 2010/0102814 A1 | 4/2010 | Satrango | |
| 2011/0113555 A1 | 5/2011 | Smith | |
| 2011/0226260 A1 | 9/2011 | Eder | |
| 2012/0186588 A1 | 7/2012 | Wilson et al. | |
| 2013/0131497 A1* | 5/2013 | Linz | A61G 1/00 5/601 |
| 2014/0232406 A1 | 8/2014 | Everett | |

FOREIGN PATENT DOCUMENTS

| | | | |
|---|---|---|---|
| JP | 2007054143 A | 3/2007 | |
| JP | 2015039461 A | 3/2015 | |
| WO | WO-2013046097 A2 * | 4/2013 | ......... A61G 13/1285 |

* cited by examiner

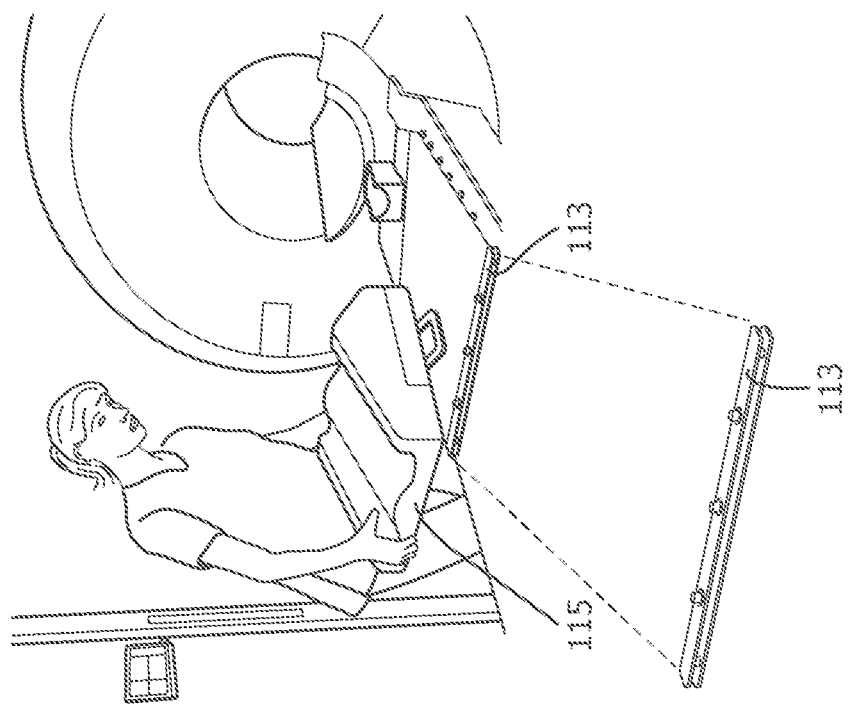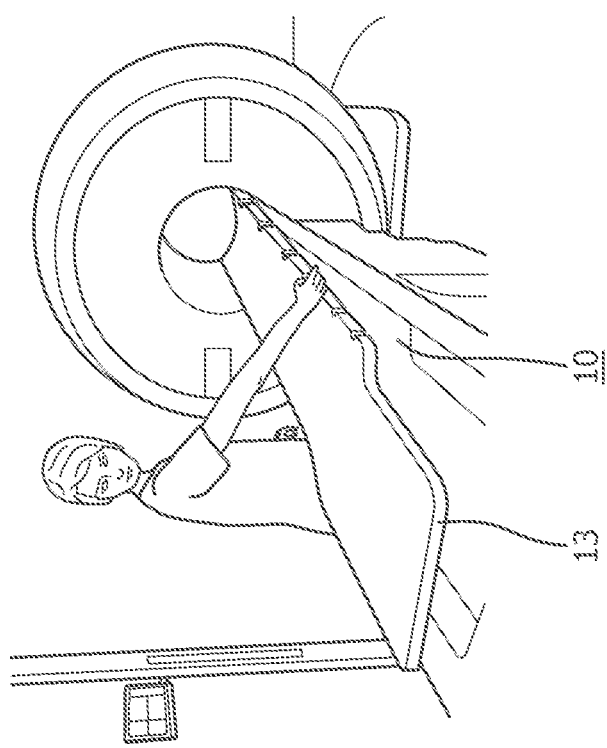
FIG. 1

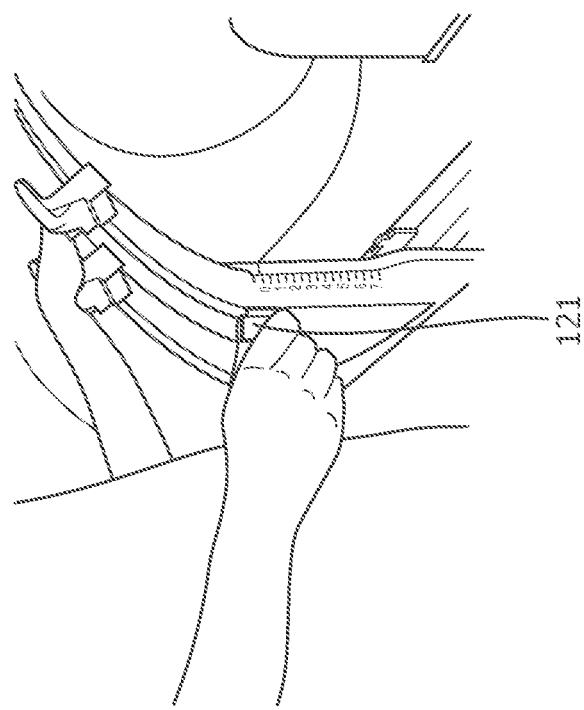
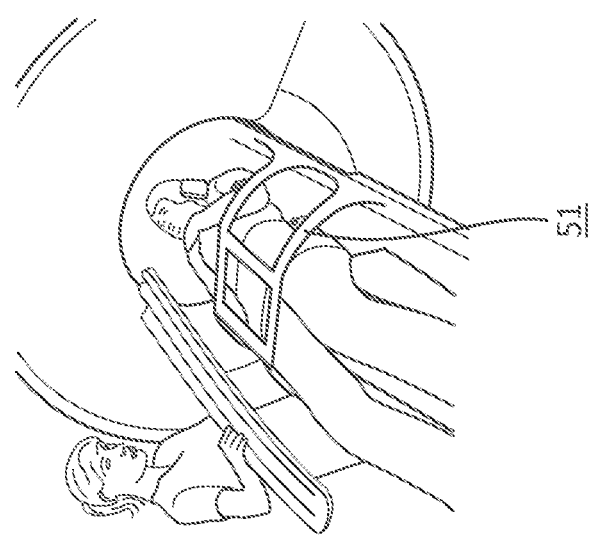
FIG. 2

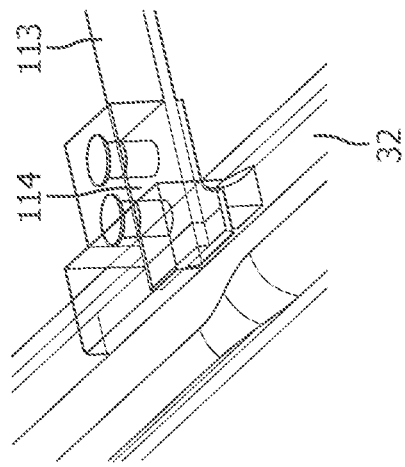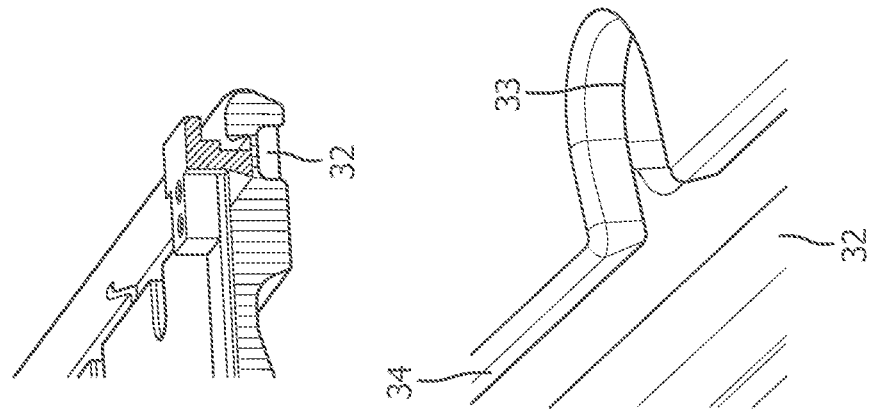
FIG. 7

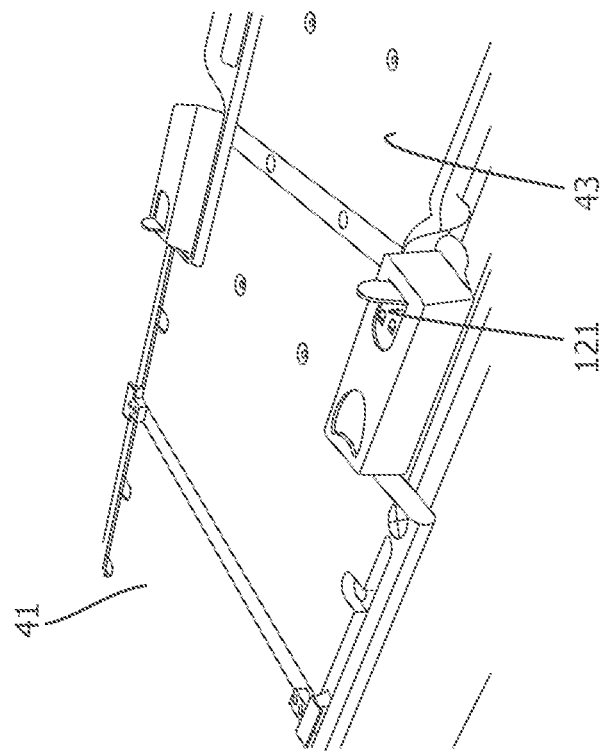
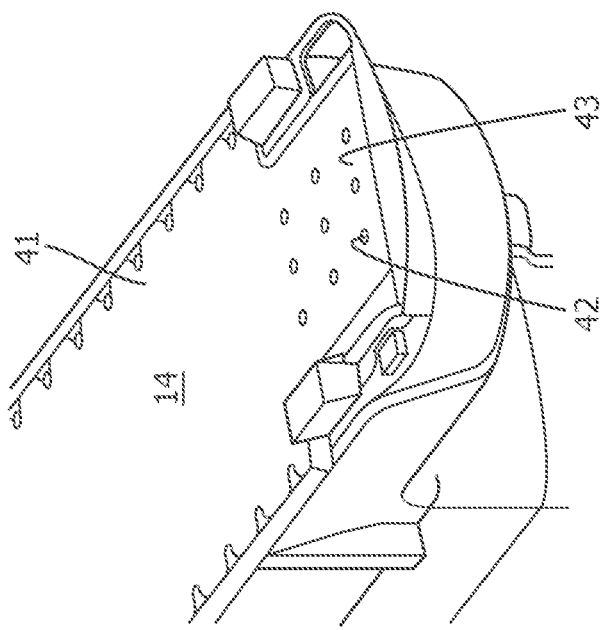
FIG. 8

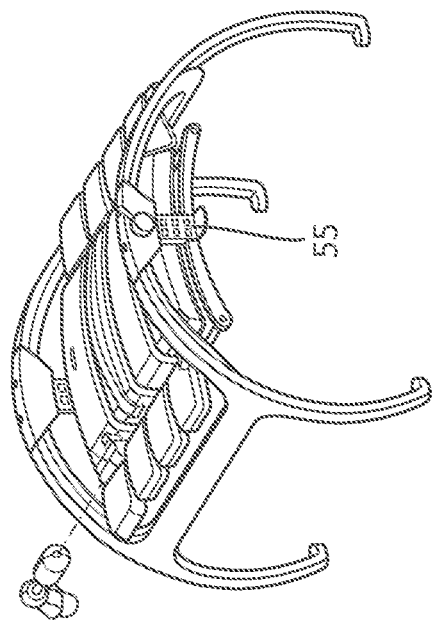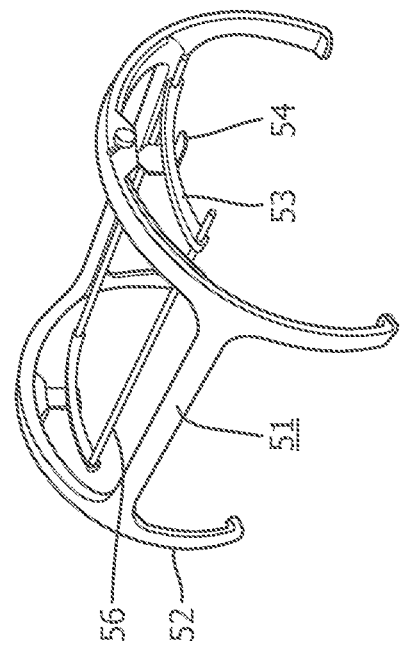
FIG. 9

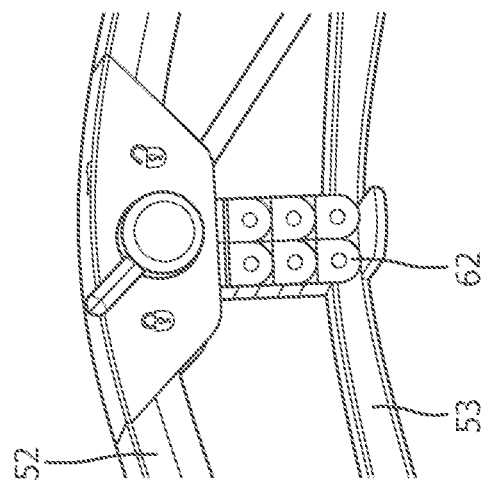
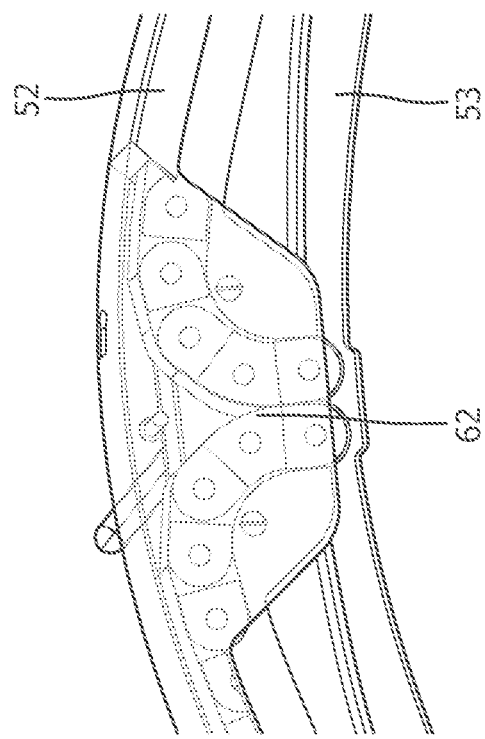
FIG. 10

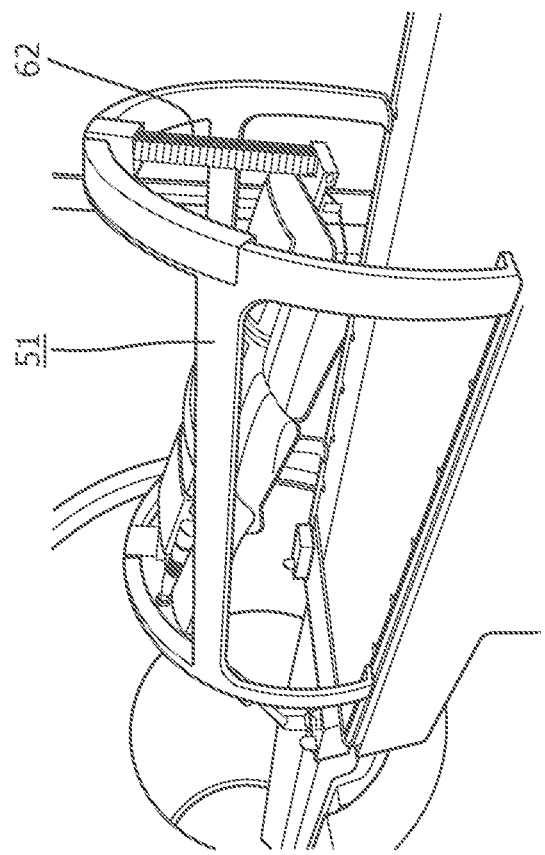
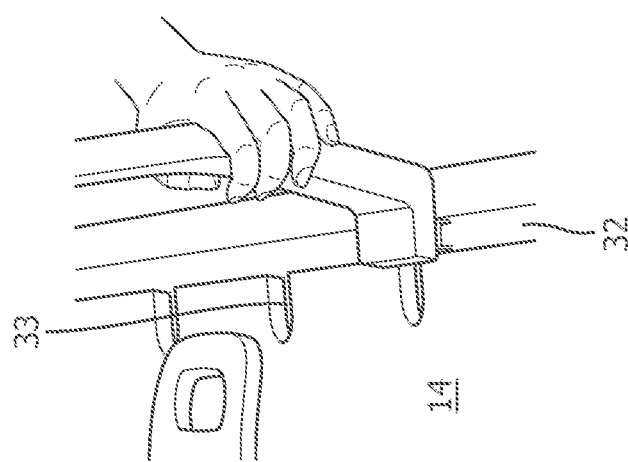
FIG. 13

PATIENT TABLE ASSEMBLY

CROSS REFERENCE TO RELATED APPLICATIONS

This application is a U.S. national phase application of International Application No. PCT/EP2016/054676, filed on Mar. 4, 2016, which claims the benefit of U.S. provisional Application Ser. No. 62/128,073 filed Mar. 4, 2015 and EP Application Serial No. 15179258.7 filed on Jul. 31, 2015 and is incorporated herein by reference.

FIELD OF THE INVENTION

The invention pertains to a patient table top assembly having a planar table top with a flat support surface to bear a patient to be examined on the basis of magnetic resonance imaging for radiotherapy planning.

BACKGROUND OF THE INVENTION

A couch top for supporting a patient during treatment is known from the U.S. Pat. No. 5,806,116.

The known couch top is a rectangular panel in which several pairs of indentations are placed in opposite side edges of the panel. An accessory device e.g. a flat index bar can be attached to the couch by way of with fastening members that fit into the indentations. Such a flat index bar is known per se from the U.S. Pat. No. 6,616,237. The known diagnostic MRI table typically has a concave lateral cross-section, and the current state-of-art RT table solution for magnetic resonance imaging employs an additional flat table top overlay that can be positioned on top of the (standard) diagnostic imaging table.

SUMMARY OF THE INVENTION

An object of the invention is to provide a patient table assembly with which an improved the MR image quality is achieved.

This object is achieved in the patient table of the invention comprising
   a curved base plate,
   a support face arranged over the curved base plate's concave side,
   a planar table top removable placed over the support face and
   the planar table top having a flat support surface opposite from the support face,
   the planar table top being contiguous to the support face.

The present invention aims at providing a patient table that is suitable for radiotherapy planning on the basis of MR image data. The MR image data in the form of magnetic resonance signals are acquired by an magnetic resonance examination system. The patient to be treated is positioned in an examination region of the magnetic resonance examination system in accurately the same position on the patient table as the position on the patient table during the actual radio therapeutic irradiation in a radiotherapy system. To facilitate accurate positioning on the patient table for radio therapy planning on the basis of magnetic resonance images, a planar table top is used. The same or a similarly shaped planar table top is also used the support the patient during irradiation. Further, arrangements for immobilization of the patient, such as a head-rest, an immobilization mask or straps can be connected to the planar table top. The arrangements for immobilization aid to position the patient in the same position and orientation on the planar table top both for MR imaging for radiotherapy planning and for the irradiation treatment.

An insight of the present invention that a drawback of the known diagnostic MRI table is its large overall thickness of the diagnostic curved table top and flat table top overlay arrangement. In the current invention the planar table top is mounted contiguously to the support face, so that the patient table with the planar table top requires less space in the bore of a magnetic resonance examination system in the configuration for radiotherapy planning as in the arrangement consisting of general diagnostic magnetic resonance table top with the additional flat overlay. In between the curved base plate and the support face there is room to accommodate a posterior RF receive coil array. The thinner planar table top structure of the invention reduces distance between the region to be imaged of the body of the patient to be examined and the posterior RF receive coil array and thus improves the MR image quality. For example the planar table top' thickness ranges from 7 mm at its outer edges to 45 mm at its centre. A thickness in the range of 7-45 mm, is considered 'thin' in the field of magnetic resonance imaging. To achieve sufficient strength of the thin planar table top of the invention, the table top has a central foam core that is covered with fibreglass cover layers on its surfaces. Suitable fibreglass is e.g. made out of Kevlar or other suitable fibre material. Carbon fibre, however, is not suitable in magnetic resonance imaging because of its high electrical conductivity. The planar table top strength is quantified in that a weight of 250 kg loaded on the planar table top causes a deformation of at most 1 mm.

Another aim of the present invention is to provide a patient table assembly that is optimized for both MR imaging for radiotherapy planning as well as for general diagnostic MR imaging. A further aim of the present invention is that the patient table assembly can be easily configured for radiotherapy planning imaging as well as for general diagnostic imaging. To that end, in this aspect of the invention a patient table assembly is provided that has a removable planar table top and a removable curved table top that can be positioned on the support face. That is, the patient table assembly has a common curved base plate and a common support face arranged over the curved base plate. The planar table top and the curved table top can be easily exchanged when alternating between radiotherapy planning and general diagnostic MR imaging. The curved table top has a shape that corresponds to the inner shape of the magnetic resonance examination system's bore so that the curved table top enables the patient to be examined to be accurately positioned such that the magnetic resonance examination system's iso-centre falls within the region-of-interest of the patient's anatomy. Accordingly, the part of the patient to be imaged is located in the region of the examination zone in which the main magnetic field is spatially very uniform and the gradient magnetic fields are very close to linearity. In this configuration optimal spatial encoding of the magnetic resonance signal is achieved which leads to optimal image quality of the reconstructed magnetic resonance image.

These and other aspects of the invention will be further elaborated with reference to the embodiments defined in the dependent Claims.

In a preferred embodiment, longitudinal grooves are provided along the longitudinal sides of the flat support surface of the planar table top. The longitudinal direction is along the long axis of the patient table. The grooves have indentations, such as notches, that extend laterally into the flat support face. Preferably, the grooves run along the outer edges of the planar table top, with the indentations integrated in the inner wall of the groove and extending into the flat support surface. Notably, the grooves are provided into the top surface of the planar table top close to the sides. The combination of the grooves along the outer edges of the planar table top, and the indentations extending from the groove's inner wall renders straight side surfaces of the planar table top. These straight side surfaces allow the planar table top to tightly fit in the magnetic resonance examination system's magnet bore. Auxiliary equipment such as an immobilization device, coil bridge or indexing bar can be mounted on the planar table top. A coil bridge is known per se from the US-patent application US2012/0186588A1. The auxiliary equipment has (a) mounting element(s) that fit(s) narrowly into the indentation, so that the mounting element clamps into or can be locked firmly into the indentation. Preferably, the groove has a (slightly) V-shaped inner edge which forms an additional surface for locking the mounting element of the auxiliary equipment, notably an indexing bar. Good results are achieved when the opposite inner edges are at an angle in the range of 10°-20°; notably at an angle of 15° very good mechanical stability is achieved. In a particular embodiment, one of the inner edges is parallel to the normal to the flat support surface and the opposite edge is at the angle in the range of, notably at the angle of 15°. A V-shape groove having a 15° renders the planer table top of the invention backward compatible with a wide range of existing auxiliary equipment. Preferably, the indentations or notches are arranged along the longitudinal grooves so that the auxiliary equipment can be locked at different positions along the planar table top, This allows to take variations of the patient's size and variations of parts of the anatomy to be imaged for radiotherapy planning into account when positioning the auxiliary device mounted in the appropriate notch, or pair of opposite notches on the planar table top. The indentations may be regularly spaced along the longitudinal grooves, e.g. at equal intervals between neighbouring indentations.

In another example of the planar table top of the invention, the support surface is formed as rectangular main support surface with a narrower end support section extending at one of its longitudinal ends. The narrower end support section leaves space for features mounted a near the end of the patient table, such as coil connector sockets into which local (surface) receiver RF coil (arrays) can be electrically connected. The end support section has a plurality of holes in its surface, preferably arranged in pairs. The mounting elements of the auxiliary equipment, e.g. an indexing bar, fit into these holes. End support sections may be provided at both longitudinal ends of the main support section. In an example, only one of these end support sections is provided with the plurality of holes. Hence, the auxiliary equipment can be mounted at the longitudinal end of the planar table top, even if the longitudinal groove and indentations extend only along the main support section's longitudinal sides.

Another object of the present invention is to provide a coil bridge which can be employed with the patient table (assembly) of the invention. The coil bridge supports an anterior RF coil (array) so that this anterior RF coil array does not need to be supported by the patient's body. In this way the patient's body is not deformed during radiotherapy planning in the magnetic resonance examination system. Thus, the shape of the patient's body is essentially equal during radiotherapy planning and the actual radiation treatment. Notably, the coil bridge of the invention avoids deformation of the patient's body due to the anterior RF coil array. The support structure with the arch-shaped members can be placed on the planar table top over the patient to be treated during radiotherapy planning. The arch-shaped members have mounting elements that fit into the grooves to be firmly mounted to the planar table top. Thus the coil bridge can be positioned freely along the longitudinal direction. The mounted elements can be clamped into the groove. To support the anterior RF coil array a coil holder is provided. The coil holder is suspended form the support structure so that its distance to the patient's body can be adjusted. In this way the anterior RF coil array can be placed close to the region of interest so as to achieve a high signal-to-noise ratio of the acquired magnetic resonance signal, but avoid the patient's body to be deformed by the anterior RF coil array. More in detail, the coil holder has an elongate centre piece that is adjustably mounted to the arch-shape member. Notably, the adjustable mounting enables that the distance of the elongate centre piece from the arch's top (apex) to be varied. This is achieved by an adjustable connector to couple the elongate centre piece to the arch-shaped member. In this way the coil holder with the anterior RF coil array can be positioned with respect to the patient's body. The elongate centre piece is orientated transverse to the longitudinal axis of the planar table top. Further, the coil holder has one or more support rods mounted to the elongate centre piece. These rods are orientated along the longitudinal axis of the planar table top. Further, these support rods can slide relative to the centre piece, so as to adjust the anterior RF coil array carried by the coil holder along the longitudinal direction of the planar table top and relative to the patient's body. Notably the arch-shape corresponds with the inner shape of the magnet bore so that efficient use of the available bore space is made when the patient table with the coil bridge is positioned into the magnet bore.

Preferably, a very stable mechanical arrangement is achieved by employed two or move arch-shaped members, each with an elongate centre piece suspended from it and two or more support rods extending between the respective elongate pieces. Notably, the respective elongate centre pieces are independently suspended for their respective arch-shaped members. Thus, the coil holder with the anterior RF coil array may be tilted simply by adjusting the distances to the arch-top of each of the elongate centre pieces to be different. In this way the anterior RF coil array can be positioned and orientated more accurately with respect to the patient's body during radiotherapy planning.

The adjustable connector may be formed by a pull chain and a locking mechanism. This provides a simple mechanically reliable adjustable connection of the elongate centre piece to the arch-shaped member. Preferably, a pair of cable-chains, configured back-to-back improves stability of the suspension of the coil holder. In particular when the part of cable chains is arranged with the individual chains next to each other orientated transverse to the longitudinal axis of the planar table top, then movement in the transverse direction is counteracted.

BRIEF DESCRIPTION OF THE DRAWINGS

These and other aspects of the invention will be elucidated with reference to the embodiments described hereinafter and with reference to the accompanying drawing wherein FIG. 1 shows in the left image how an indexed flat table top is attached on top of the regular diagnostic MRI table top. Enlargement: Indexing bar creates interface for attaching PPDs to the dedicated indexed positions of the flat table.

In the right image FIG. 1 shows the user attaching knee wedge PPD to the indexing bar attached to the indexed position of the flat table;

FIG. 2 shows in the left image how a coil bridge is located over the patient and user attaches the coil on top of the bridge to avoid direct contact to the patient. The coil bridge height can be adjusted by adjusting the heights of the four legs of the bridge. Adjustment requires that the tightening screw is loosened, leg height is adjusted, and the screw is tightened again;

FIG. 7 shows details of an example of the indexing bar locking mechanism;

FIG. 8 of the invention that the planar table end section has hole pairs for fixing shorter dedicated indexing bars;

FIG. 9 shows in an example of patient table of the invention an arch shaped adjustable coil support without (left) and with anterior coil (right);

FIG. 10 shows in an example of patient table of the invention an integrated adjustment mechanics, with a pull chain (left) and the locking mechanism (right);

FIG. 13 shows in an example of patient table of the invention the coil bridge on top of the planar table top with coil supported (right);

DETAILED DESCRIPTION OF THE EMBODIMENTS

Figure 3:
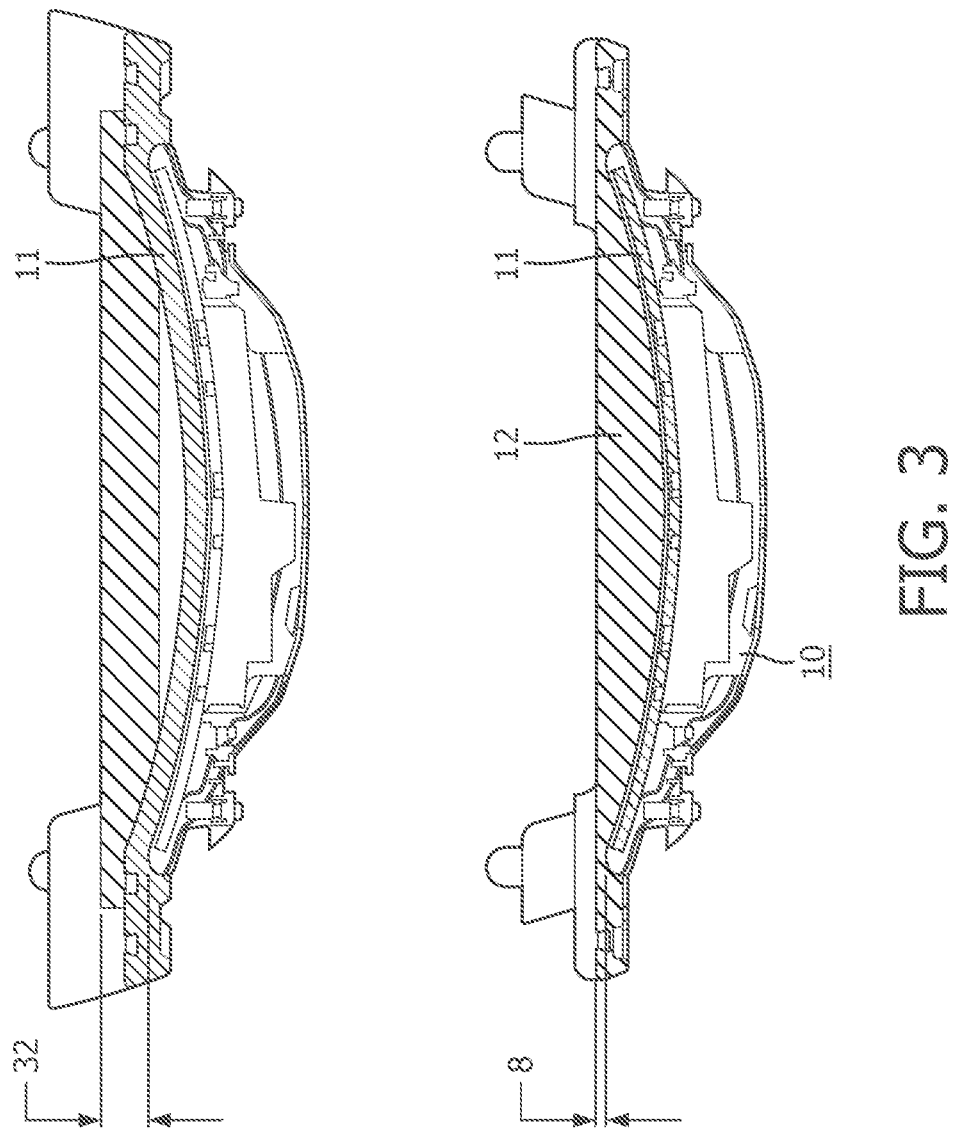
FIG. 3 shows the cross-sections of the known MR-RT solution with the additional overlay on the diagnostic table and for comparison the merged flat table top solution.

In modern radiation therapy (RT) the radiation dose is planned on 3D images. CT is the most common imaging method used for dose planning purposes (step often referred as CT simulation), but MRI imaging is getting more and more popular due to superior soft tissue contrast. The prerequisite for the use of MRI images is that the patient is positioned similarly during the simulation imaging and RT treatment to ensure that the patient anatomy in the planned images corresponds as good as possible to the patient anatomy during the therapy. Due to this reason the patient is typically positioned on a flat table surface during the imaging and radiation therapy. Furthermore, dedicated patient positioning devices (PPD), such as knee wedges, head mask, head rest, etc., are often used to help repeated positioning of the patient in the same way. This requires that a flat table surface allowing the use of patient positioning devices in controlled (indexed) locations is arranged in the MRI environment. A further requirement for the simulation imaging in the MRI environment is the need of arranging receiving MRI coil set-up in a way that the MR image quality is sufficient for the simulation use, while the coil set-up does not affect the patient anatomy, e.g. by modifying the body contour shape, and does allow the use of PPDs.

The known solution uses the indexed thin flat table top overlay that can be positioned on top of the standard diagnostic imaging table, see FIG. 1. FIG. 1 shows in the left picture that a planar table top 13 is positioned on top of the standard diagnostic imaging table 10. In the right picture it is shown that an indexing bar 113 is placed on top of and across the planar table top 13. On the indexing bar for example a patient head rest 115 is placed. Selection of PPDs, such as knee wedges are available, and those are attached to the indexed position of the flat table overlay using indexing bars, see FIG. 1. The indexing bar is shown in the enlargement. FIG. 1 shows in the right image how an indexed flat table top is attached on top of the regular diagnostic MRI table top. The indexing bar creates an interface for attaching PPDs to the dedicated indexed positions of the flat table. In the right image, FIG. 1 shows the user attaching a knee wedge PPD to the indexing bar attached to the indexed position of the flat table.

Usually two coils are used when imaging in the body area. One coil is the posterior coil integrated under the diagnostic patient table top, and the other is the anterior coil located on top of the patient. In the diagnostic imaging anterior coil is located directly on top of the patient, while in the MRI simulation imaging the anterior coil is located on top of the coil bridge in order to avoid the body contour shaping, see FIG. 2. FIG. 2 shows in the left image how the coil bridge 51 is located over the patient and user attaches the coil on top of the bridge to avoid direct contact to the patient. The coil bridge height can be adjusted by adjusting the heights of the four legs of the bridge. Adjustment requires that a tightening screw 121 is loosened, leg height is adjusted, and the screw is tightened again, as shown in the right hand picture.

An insight of the present invention is that the image quality is insufficient in the body region, and that the usability of the coil bridge is not good enough. The main reason for the lowered image quality is the decreased SNR caused by the flat table top overlay increasing the distance from the patient to the posterior coil and the bridge increasing the distance from the patient to the anterior coil. The lower SNR complaint is also related to the usability of the coil bridge height adjustments. Due to the poor usability of the four separately adjusted legs, customers are not able to minimize the distance of the anterior coil to the patient. The present invention proposes solutions that decrease the distance between the coil and the patient, improve the usability of adjusting the anterior coil position, while offering indexed flat table surface and indexing bars compatible with the PPDs available on the market.

One aspect of the invention is a new planar table top solution. Instead of using the planar table top overlay on top of the diagnostic MRI table, the invention proposes to make dedicated planar table top that replaces the diagnostic table. This gives several advantages.

Figure 16:
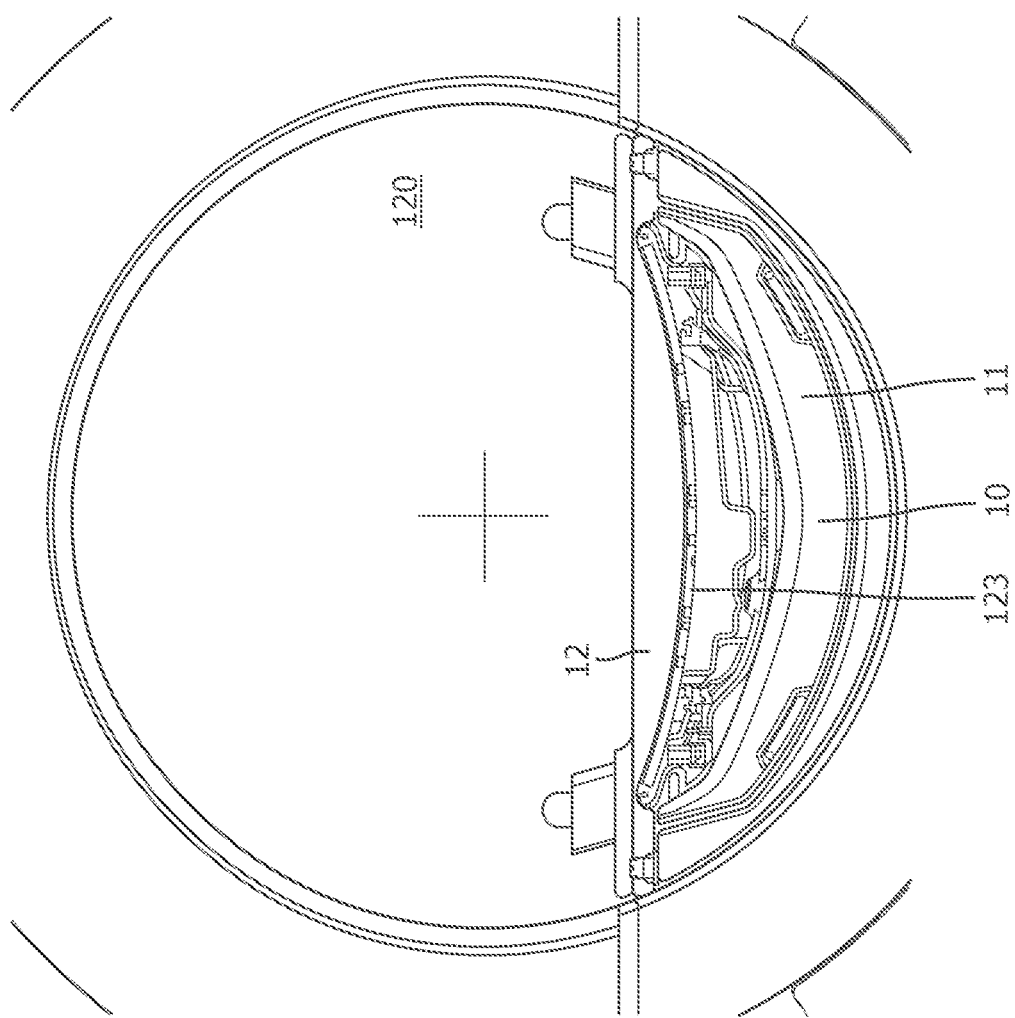
FIG. 16 shows a cross sectional view of the an example of patient table and posterior coil and support surface for the patient table of the invention mounted in an magnetic resonance examination system's bore.

The sizes of the mechanical structures and material thicknesses can be optimized for thinner structure, when there is no need for the two individual pieces to have sufficient mechanical strength. This is shown in more detail in FIG. 16. FIG. 16 shows a lateral (i.e. orthogonal to the longitudinal axis of the patient table, cross section of the planar table top mounted in the patient table assembly. At the centre (labelled 'A') the thickness of the planar table top is 44 mm, which adds to achieve at most 1 mm deformation when a load of 250 kg is applied on the planar table top. At the sides (labelled 'B'), the thickness is only 8 mm. The planar table top is built up from a foam core, which is light which is covered with fibreglass, e.g. Kevlar, for mechanical strength.

The curvature of the diagnostic MRI table is not constraining the creation of the flat surface. Structure can be optimized for magnet bore, patient carrier and posterior coil constraints.

Having the single planar table top structure for both diagnostic imaging as well as for radio therapy planning instead of overlay on the regular table removes potential play between the overlay and the diagnostic MR table and thus improves the accuracy of the patient table. Accuracy of the table is more important in the MR imaging for radio therapy planning (RT simulation imaging) than in the diagnostic imaging.

FIG. 3 shows in the top picture a cross-sections of the known MR-RT solution with the additional overlay on the diagnostic table and for comparison the merged planar table top solution. FIG. 3 shown in the bottom picture a cross section of an example of the patient table 10 of the invention. Over the curved based plate 11, the support face 12 is placed over the curved base plate's concave side. As shown in FIG. 3, the invention reduces the vertical size of the patient table by about 24 cm, because more efficient use is made of the space at the concave side of the curved base plate.

Figure 4:
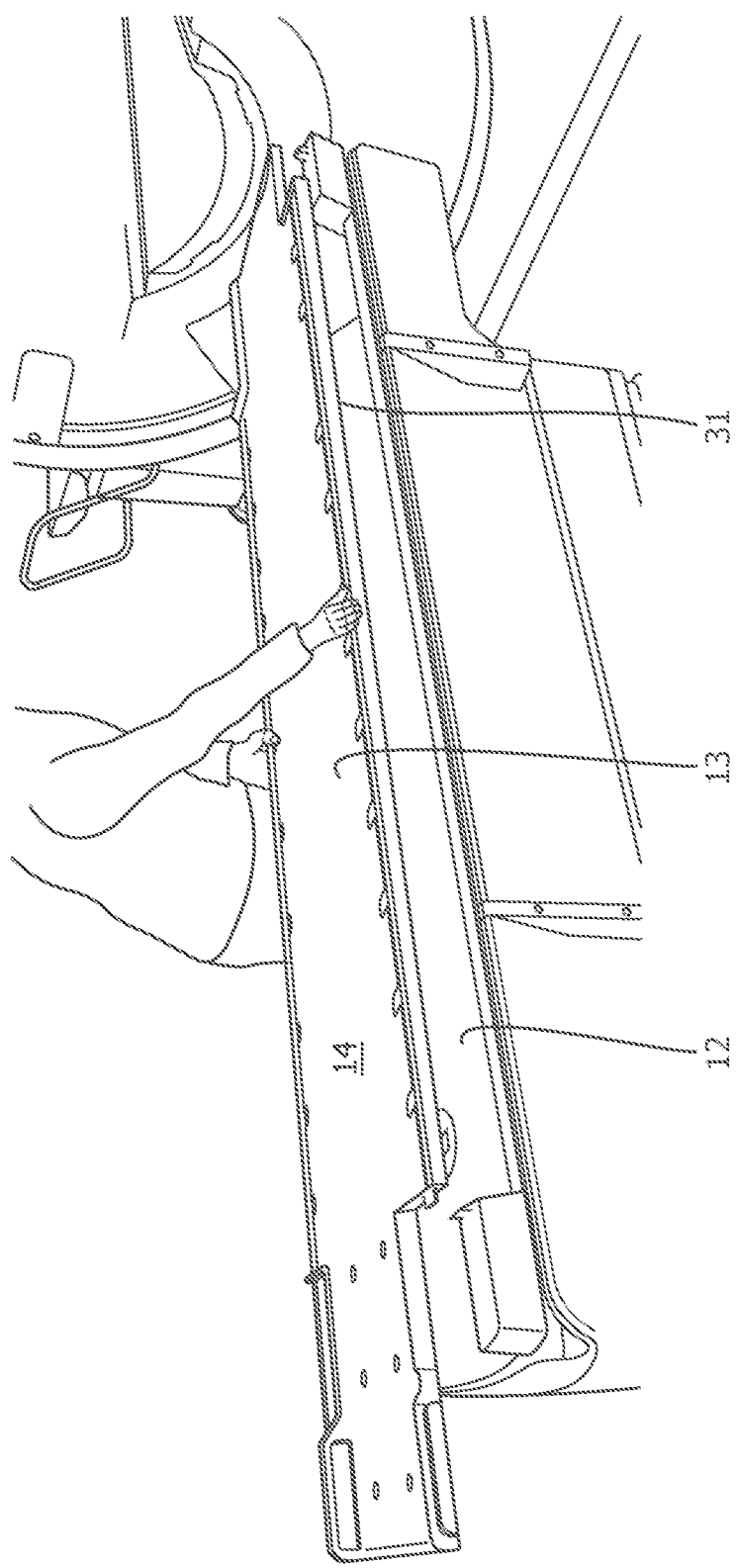
FIG. 4 shows a user attaching/removing the flat table top of the invention from the carrier.

Another aspect of the invention is that both the diagnostic and planar table top are easily removable from the carrier by the user, see FIG. 4. This is important as in many cases MRI is used both in diagnostic and RT simulation imaging use. Thus user needs to be able to switch quickly between the two table tops. In order to facilitate this, the planar table top has been made light-weighted. FIG. 4 shows a user attaching/removing the planar table top of the invention from the carrier. The user places the planar table top 13 on the support face 12. The Figure also shows that the longitudinal sides 31 fit closely to the edge of the bore of the magnetic resonance examination system 120.

Figure 5:
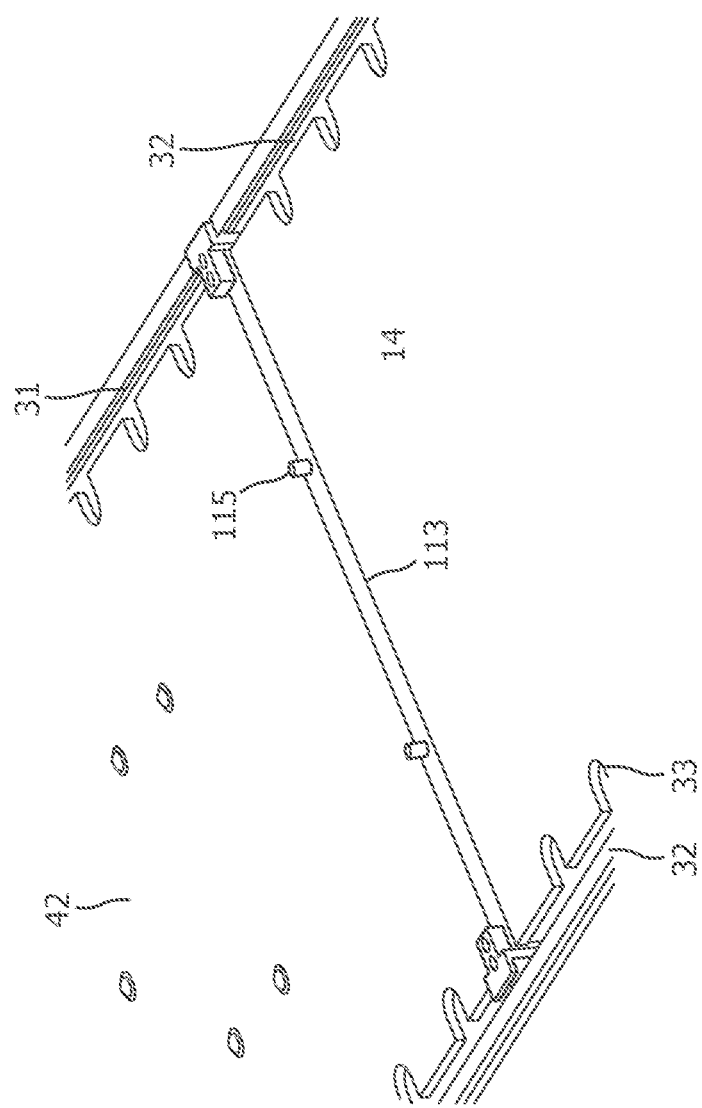
FIG. 5 shows an example of the notched indexing solution of the invention based on grooves and regularly spaced notches close to the sides of the flat table top.

Another aspect of the new planar table top solution is the new notched style indexing solution. The solution is based on having longitudinally extending grooves with regularly spaced (14 cm spacing) notches on the top surface of the planar table top close to the sides, see FIG. 5. FIG. 5 shows an example of the notched indexing solution of the invention based on grooves and regularly spaced notches close to the sides of the planar table top. FIG. 5 shows a bird's eye top view of the patient table 10. On top of the planar support face 14 the indexing bar 113 is placed across the patient table. Along the longitudinal sides 31 the longitudinal grooves 32 extend. At regular intervals the indentations 33, in the form of notches are disposed into which the indexing bar 113 can be clamped. The indexing bar has a number of pins 115 are provided onto which PPDs can be mounted. Further, holes 42 are provided in the planar table top to hold PPDs.

Figure 6:
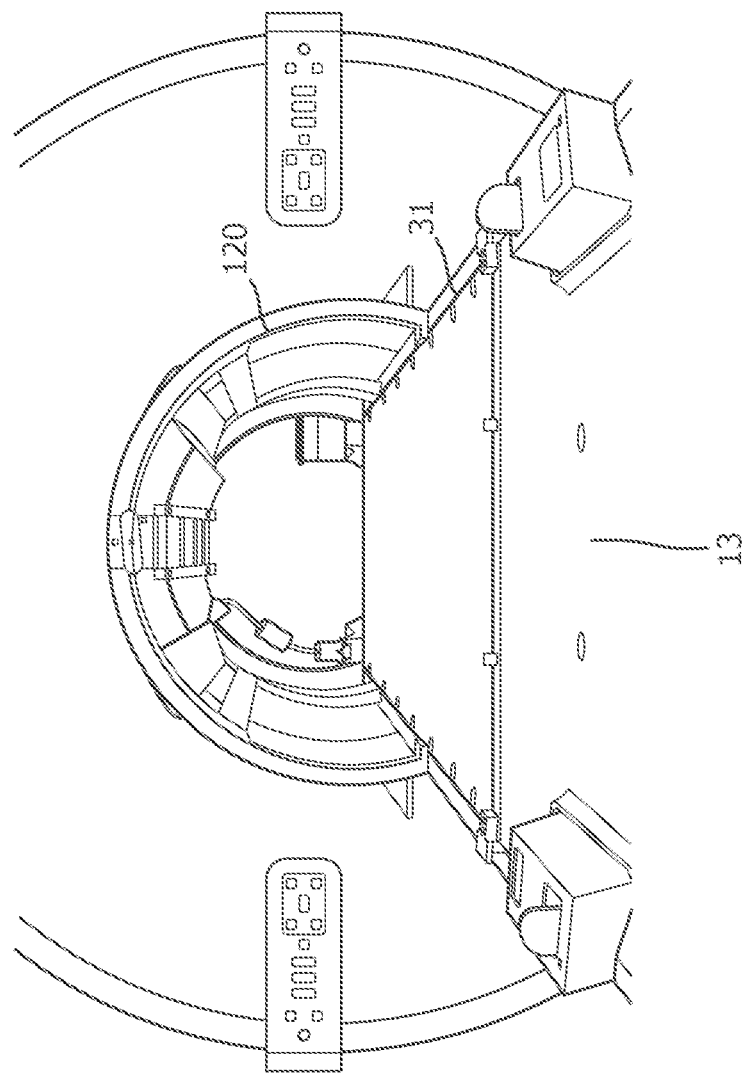
FIG. 6 shows and example of a planar table top of the invention fitting tightly to the MRI bore.

FIG. 6 shows and example of a planar table top 113 of the invention fitting tightly to the MRI bore 120. The planar table top of the invention has been designed to have straight surfaces 31 tightly fitting to bore, see FIG. 6. The solution of the invention where the indexing is on the top surface of the planar table reduces chance of finger pinching or other hazardous situations as well as creates room for accessories to be attached to the indexing notches or grooves. Another benefit of the new indexing solution is that the groove creates additional surfaces that can be used for creating better attachment of the indexing bar (discussed in more detail below). Yet another benefit of the new indexing solution is that the grooves can be used for attaching other tools, such as coil bridge, independent of the indexing notch locations freely along the distance of the planar table top (discussed in more detail below).

Another part of the invention is the new indexing bar design. The indexing bar includes middle bar with two or more pins 115 for attaching PPDs. The mechanism locking the indexing bar to the indexed location is novel. It utilizes the notch 33 and the groove 32 for creating accurate and reliable indexing, see FIG. 7. The groove 32 has slightly v-shaped inner edge 34 which is used as an additional surface for locking the indexing bar in the indexed location. The prior art utilizes only the surfaces of the notch itself for this purpose, see for example the U.S. Pat. No. 6,616,237. Advance in this kind of solution of the invention is better perpendicular guidance for indexing bar related to the table side. FIG. 7 (top right part) shows details of an example of the indexing bar locking mechanism. The locking mechanism 114 extends beyond the notch to create locking utilizing the v-shaped inner surface 34 of the groove 32. There is also part extending to the notch fixing the location in the longitudinal direction.

Another new innovation is the utilization of the whole table length for PPDs. The coil connectors located at the corners of the patient table prevent fully rectangular planar table top design. At the ends the planar table top structure is narrower, thus preventing the use of the indexing bars designed for notched and grooved section, see FIG. 8. In order to overcome this, table end has three pairs of holes 42. These holes receive dedicated indexing bars, that mate to the holes and have two pins upwards for attaching PPDs, see FIG. 8. The locations of the holes have been selected so that the longitudinal distance continues the 14 cm spacing from the grooved and notched section. As a result all the indexing bars, regardless if they are notched and grooved style indexing bars for the middle section or the shorter end section style indexing bars, match the 14 cm spacing of the indexing locations. Consequently, the indexing created on the new planar table solution with narrower end sections can be transferred to the RT treatment table having rectangular table shape and 14 cm-scaped indexing extending over the whole length of the table.

FIG. 8 shows in an example of patient table of the invention that the planar table end section has hole 42 pairs for fixing shorter dedicated indexing bars. Locations of the holes 42 have been selected so that the indexing spacing continues from the notched and grooved section. The version of the patient table of the invention of FIG. 8 has a main rectangular support section 41 and an end support section 43. The end support section's width is small than the main rectangular support. This provides space for further equipment or functional structure such as a coil connector 121.

Figure 11:
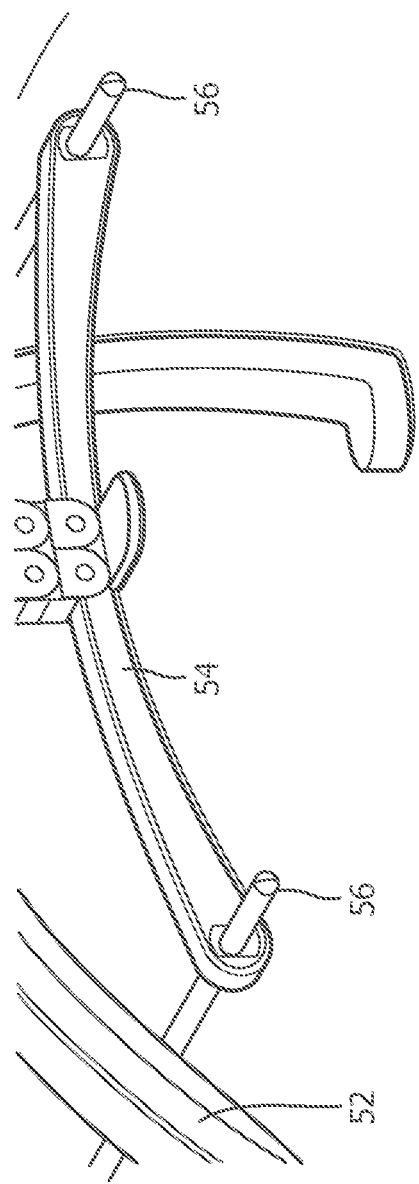
FIG. 11 a sliding mechanism of the support rods of the centre piece.

FIG. 9 shows in an example of patient table an arch shaped adjustable coil support without (left) and with anterior coil (right). Part of the innovation is the new coil bridge 51 having an arch shaped fixed frame fitting to the shapes of the magnet bore and an adjustable centre piece hanging from the frame, see FIG. 9. The coil (not shown) when mounted to the coil holder is located on top of the centre piece, and the height of the centre piece can be adjusted from the both ends. The coil holder is formed by the elongate centre pieces 53 at each of the arch shaped members (arches) 52 and the rods 56. The height adjustment is implemented with a pair of pull chains 62 integrated inside the arch shaped frame 51 within the arches 52 at the both longitudinal ends. The pull chain 62 is constructed of plastic cable chain, exploiting the shape on both sides of the arch, which enables the height adjustment of the elongate centre piece forming an interface piece between the pull chain 62 and the arches, connected to other end of the pull chain, see FIG. 10. FIG. 10 shows in an example of patient table 10 an integrated adjustment mechanics, with a pull chain 62 (left) and the locking mechanism (right). The pull chain 62 can be locked via locking mechanism with small force, there is one locking mechanism per arch. The elongate centre piece 53 connected to the pull chain 62 provides platform, and enables the sliding of the support rods 56 when the interface pieces of the arches are at different height, see FIG. 11. FIG. 11 shows in an example of patient table of the invention a sliding mechanism of the support rods of the elongate centre piece.

Figure 12:
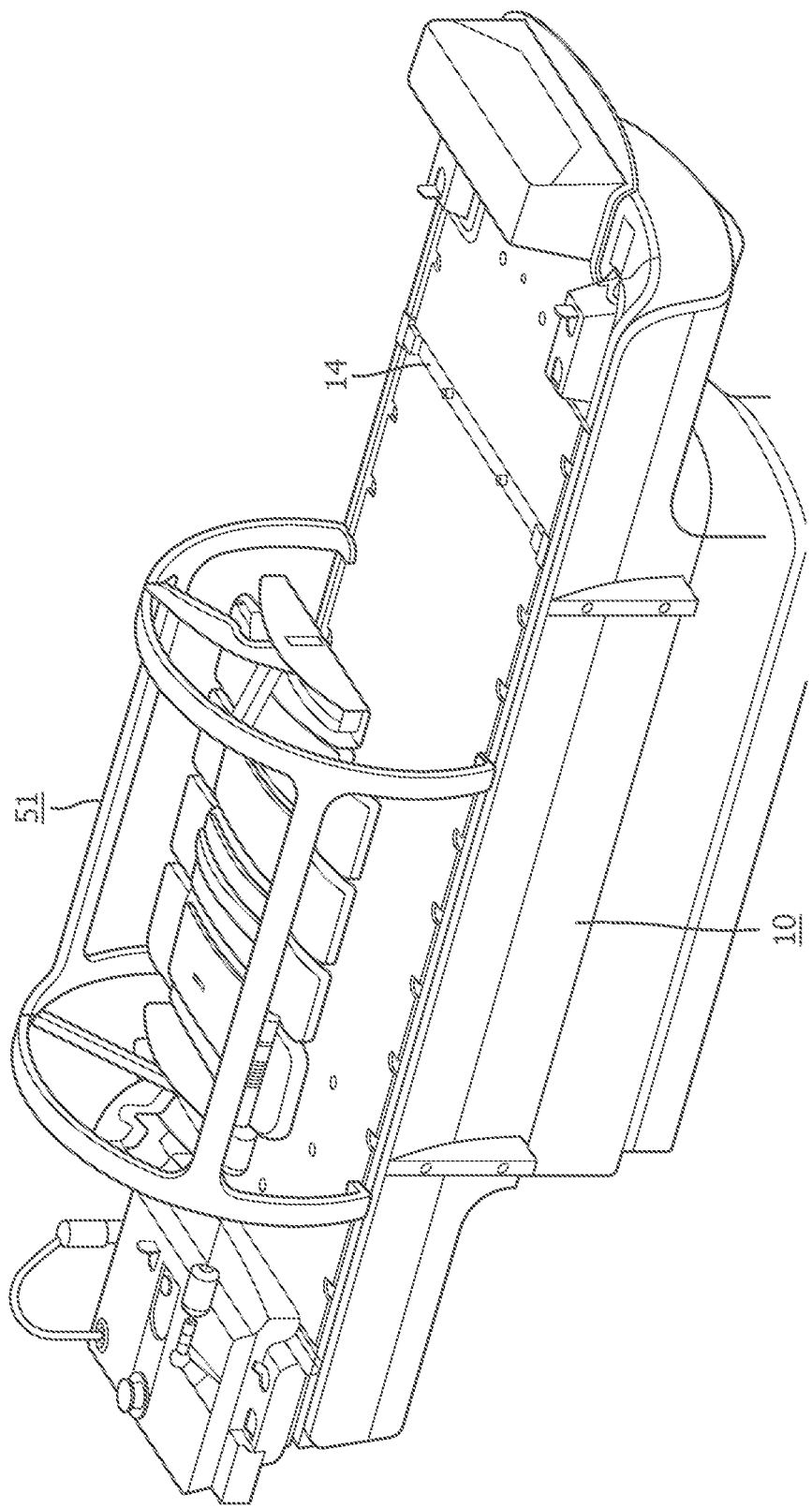
FIG. 12 shows in an example of patient table of the invention with the coil bridge on top of the planar table top.

The rods 56 are small in diameter and provide support for the coil, and the coil is hanging from the arch shaped frames via pull chain 62. The pull chain 55 has a spring mechanism to prevent the coil holder to free fall downwards when lock is opened. The frame is located on top of the new planar table top 13 utilizing grooves to prevent the bridge to drop from the table, see FIG. 12. FIG. 12 shows in an example of patient table of the invention with the coil bridge on top of the planar table top. The legs of the frame have shapes that fit in the grooves of the planar table top. The coil bridge 51 slides in the groove 32 making the adjustment of the feet-head direction position of the bridge possible.

The new coil bridge design described above allows easy coil position adjustment with the two adjustment locations. Two adjustment locations are sufficient as typically only the height and feet-head direction tilt angle of the coil needs to be adjusted. Furthermore the adjustment locations can be accessed easily from either side of the patient support. In the known coil bridge design four adjustment locations are needed and only two of them can be accessed from the one of the patient support. The advantage of the pull chain adjustment mechanism is that the structure is sufficiently rigid to prevent uncontrolled swinging of the hanging centre piece. The cable chain structure in itself prevent swinging motion in feet head direction. Having two cable chains "back-to-back" prevents swinging motion in left-right direction.

FIG. 13 shows in an example of patient table 10 of the invention the coil bridge 51 on top of the planar table top 13 with coil supported (right). The coil frame snap fit attachment to accessory groove is also shown (left).

Figure 14:
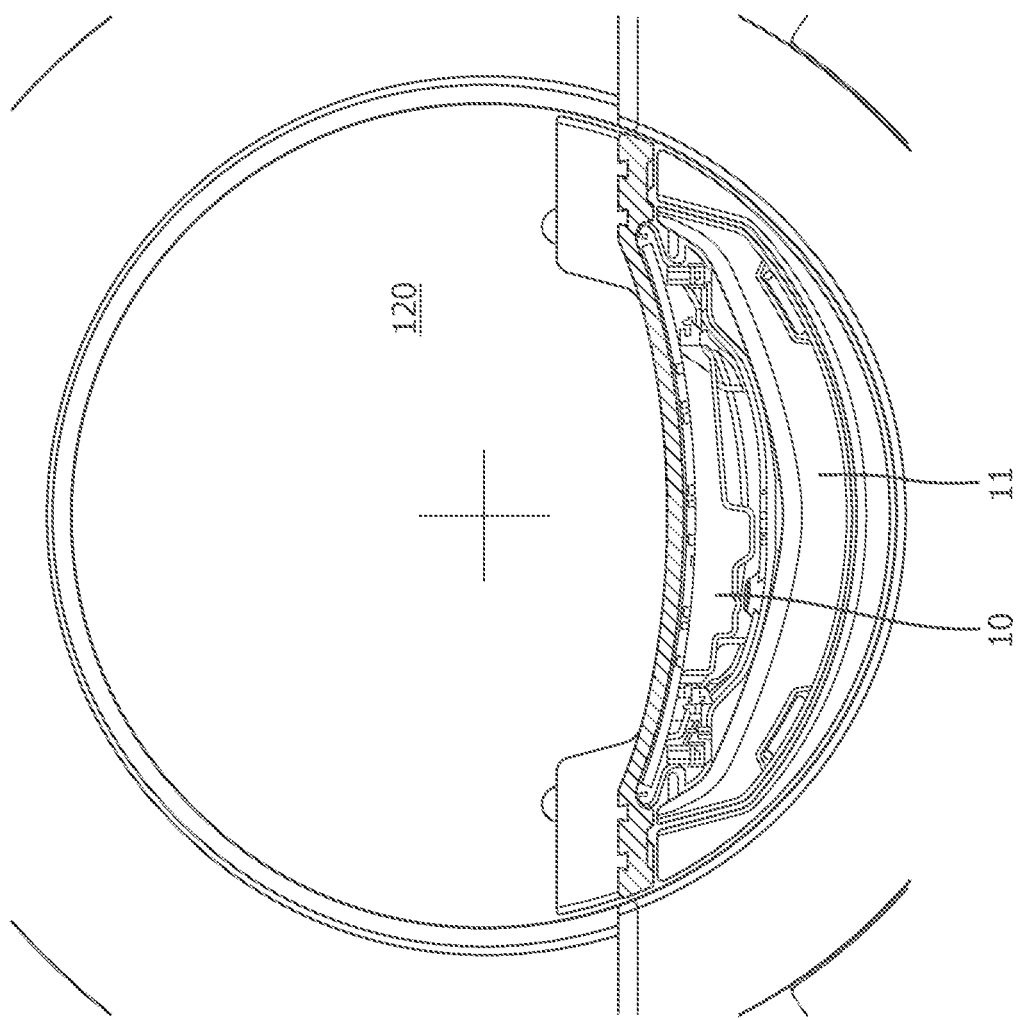
FIG. 14 shows a cross sectional view of the an example of patient table and posterior coil and support surface for the patient table of the invention mounted in an magnetic resonance examination system's bore.

FIG. 14 shows a cross sectional view of the an example of patient table 10 and posterior coil and support surface 11 for the patient table of the invention mounted in an magnetic resonance examination system's bore 120.

Figure 15:
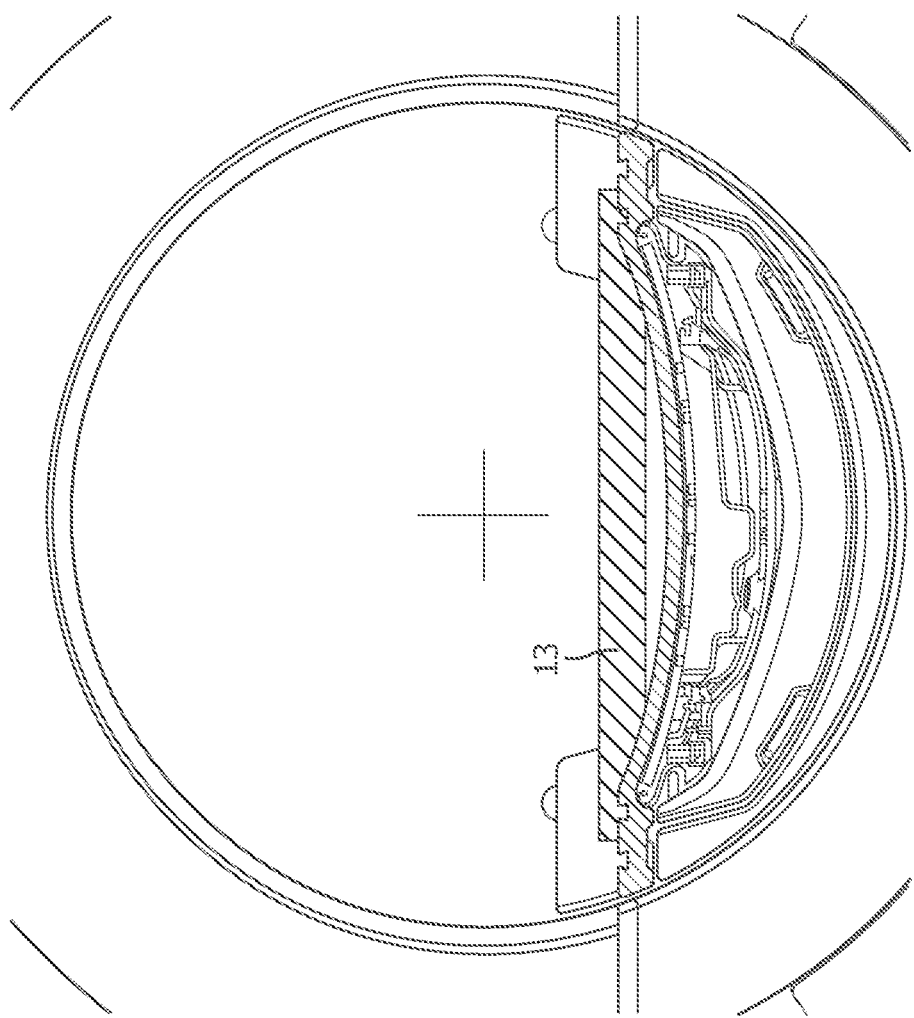
FIG. 15 shows a known diagnostic table with flat overlay is supported on diagnostic table flat surface (111 mm from iso-centre.

FIG. 15 shows a known diagnostic table with flat overlay is supported on diagnostic table flat surface (111 mm from iso-centre).

FIG. 16 shows a cross sectional view of the an example of patient table 10 and posterior coil 123 and support surface 12 for the patient table 10 of the invention mounted in an magnetic resonance examination system's bore 120. The planar table top of the invention is placed on the carrier's supporting surface.

Figure 17:
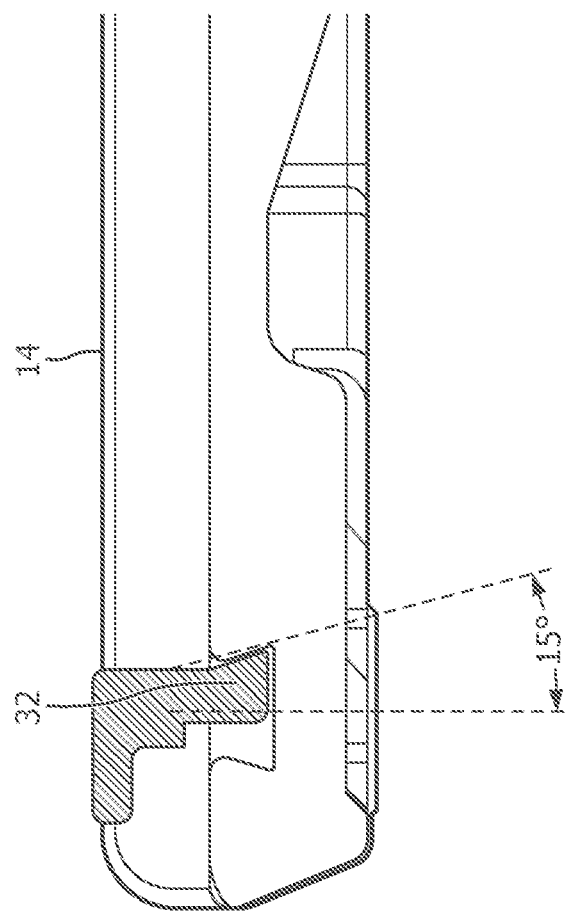
FIG. 17 shows a side elevation along cross section A-A of the groove V-shape having 15 degrees on each side and FIG. 18 shows a top view of the indexing bar support surfaces.

FIG. 17 shows a detailed cross section A-A of the groove V-shape 32 having 15 degrees on each side.

Figure 18:
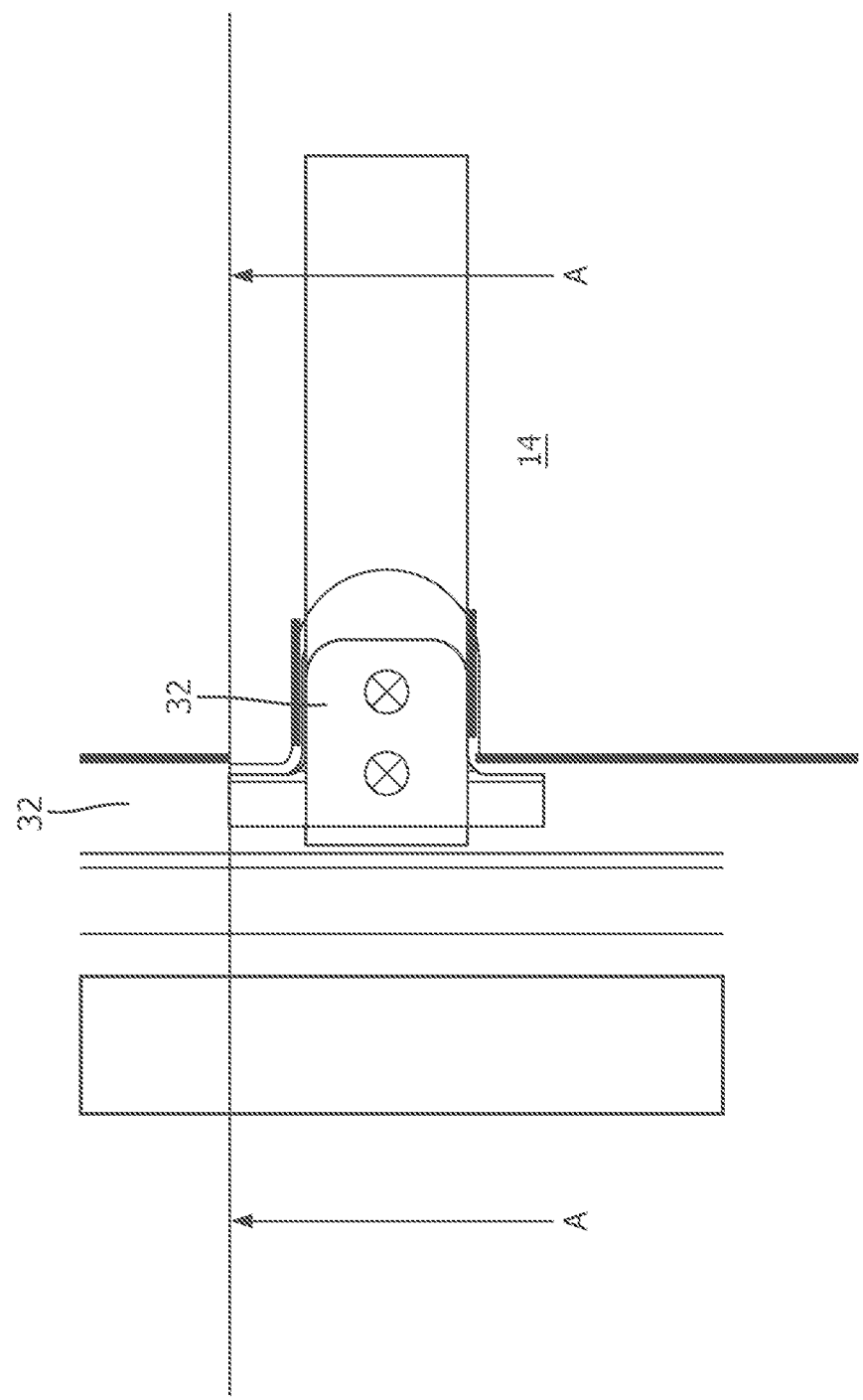

FIG. 18 shows a top view of the indexing bar support surfaces.

The invention claimed is:

1. A patient table, comprising:
 a curved base plate having a concave side;
 a support face arranged over the concave side of the curved base plate;
 a planar table top, wherein the planar table top is removably placed over the support face,
  wherein the planar table top has a flat support surface opposite from the support face, and
  wherein the planar table top is contiguous to the support face; and
 a coil bridge, the coil bridge comprising:
  a support structure having one or more arch-shaped members, and
  a coil holder suspended from the support structure, wherein the coil holder includes:
   one or more elongate center pieces adjustably mounted to the one or more arch-shaped members by an adjustable connector, and
   one or more support rods mounted transversely to the one or more elongate center pieces.

2. The patient table of claim 1, wherein the coil bridge includes:
 two or more of the arch-shaped members from each of which respective ones of the elongate center pieces are suspended; and
 two or more of the support rods extending between the respective elongate center pieces.

3. The patient table of claim 1, wherein the adjustable connector of the coil bridge includes a pull chain.

4. The patient table of claim 1, wherein the adjustable connector of the coil bridge includes a pair of back-to-back cable chains.

5. The patient table of claim 1, wherein the planar table top comprises:
 longitudinal sides with one or more longitudinal grooves provided along one or both the longitudinal sides in the flat support surface, protruding transversely to the flat support surface, and
 one or more indentations provided in the flat support surface and transverse to the one or more longitudinal grooves.

6. The patient table of claim 5, wherein the indentations are regularly spaced along the one or more longitudinal grooves.

7. The patient table of claim 5, wherein the one or more longitudinal grooves have a V-shaped inner edge.

8. The patient table of claim 5, wherein the flat support surface includes:
 a rectangular main support surface having longitudinal ends; and
 an end support section extending from at least one of the longitudinal ends of the main support surface,
  wherein a width of the end support section is less than a width of the main support surface, and
  wherein a plurality of holes is provided in the end support section, wherein the holes are arranged in pairs.

9. A patient table, comprising:
 a curved base plate having a convex side and a concave top side;
 a support face having a convex side and a flat side, wherein the support face is arranged over the concave top side of the curved base plate such that the convex side of the support face faces the concave top side of the curved base plate;
a planar table top, wherein the planar table top is removably placed over the flat side of the support face,
wherein the planar table top has a flat support surface opposite from the flat side of the support face, and
wherein the planar table top is contiguous to the support face; and
a coil bridge, the coil bridge comprising:
a support structure having one or more arch-shaped members; and
a coil holder suspended from the support structure, wherein the coil holder includes:
one or more elongate center pieces adjustably mounted to the one or more arch-shaped members by an adjustable connector, and
one or more support rods mounted transversely to the one or more elongate center pieces.

10. The patient table of claim 9, wherein the planar table top comprises:
longitudinal sides with one or more longitudinal grooves provided along one or both the longitudinal sides in the flat support surface, protruding transversely to the flat support surface, and
one or more indentations provided in the flat support surface and transverse to the one or more longitudinal grooves.

11. The patient table of claim 10, wherein the indentations are regularly spaced along the one or more longitudinal grooves.

12. The patient table of claim 10, wherein the one or more longitudinal grooves have a V-shaped inner edge.

13. The patient table of claim 10, wherein the flat support surface includes:
a rectangular main support surface having longitudinal ends; and
an end support section extending from at least one of the longitudinal ends of the main support surface,
wherein a width of the end support section is less than a width of the main support surface, and
wherein a plurality of holes is provided in the end support section, wherein the holes are arranged in pairs.

14. The patient table of claim 9, wherein the coil bridge includes:
two or more of the arch-shaped members from each of which respective ones of the elongate center pieces are suspended; and
two or more of the support rods extending between the respective elongate center pieces.

15. The patient table of claim 9, wherein the adjustable connector of the coil bridge includes a pull chain.

16. The patient table of claim 9, wherein the adjustable connector of the coil bridge includes a pair of back-to-back cable chains.

\* \* \* \* \*